(12) United States Patent
Marom et al.

(10) Patent No.: US 8,735,627 B2
(45) Date of Patent: May 27, 2014

(54) INTERMEDIATE COMPOUNDS AND PROCESS FOR THE PREPARATION OF FINGOLIMOD

(75) Inventors: Ehud Marom, Kfar Saba (IL); Michael Mizhiritskii, Rehovot (IL); Shai Rubnov, Tel Aviv (IL)

(73) Assignee: Mapi Pharma Ltd., Ness Ziona (IL)

( * ) Notice: Subject to any disclaimer, the term of this patent is extended or adjusted under 35 U.S.C. 154(b) by 0 days.

(21) Appl. No.: 13/881,961

(22) PCT Filed: Oct. 27, 2011

(86) PCT No.: PCT/IL2011/000838
§ 371 (c)(1),
(2), (4) Date: Apr. 26, 2013

(87) PCT Pub. No.: WO2012/056458
PCT Pub. Date: May 3, 2012

(65) Prior Publication Data
US 2013/0217899 A1    Aug. 22, 2013

Related U.S. Application Data

(60) Provisional application No. 61/407,483, filed on Oct. 28, 2010.

(51) Int. Cl.
*C07C 213/02* (2006.01)

(52) U.S. Cl.
USPC ........................................................ 564/357

(58) Field of Classification Search
USPC ........... 549/371; 564/356, 357; 568/648, 335, 568/13; 558/214
See application file for complete search history.

(56) References Cited

U.S. PATENT DOCUMENTS

| | | |
|---|---|---|
| 4,086,341 A | 4/1978 | Krohn et al. |
| 4,857,659 A | 8/1989 | Frenette et al. |
| 4,978,793 A | 12/1990 | Quirk et al. |
| 5,604,229 A | 2/1997 | Fujita et al. |
| 5,902,896 A | 5/1999 | Bauer |
| 5,952,316 A | 9/1999 | Fujita et al. |
| 6,284,915 B2 | 9/2001 | Hirase et al. |
| 2001/0008945 A1 | 7/2001 | Hirase et al. |
| 2006/0183707 A1 | 8/2006 | Nishikawa et al. |
| 2009/0082471 A1 | 3/2009 | Czarnik |

FOREIGN PATENT DOCUMENTS

| | | |
|---|---|---|
| CN | 1528738 A | 9/2004 |
| CN | 1765872 A | 5/2006 |
| DE | 10355169 A1 | 6/2005 |
| EP | 0989113 A1 | 3/2000 |
| JP | H11310556 A | 11/1999 |
| WO | 00/27798 A1 | 5/2000 |
| WO | 00/53569 A1 | 9/2000 |
| WO | 2005/041899 A2 | 5/2005 |
| WO | 2009/061374 A2 | 5/2009 |
| WO | 2009/133045 A1 | 11/2009 |
| WO | 2010/055027 A2 | 5/2010 |
| WO | 2010/055028 A2 | 5/2010 |

OTHER PUBLICATIONS

Astle et al., (1956) Catalysis by Anion Exchange Resins. Condensations of Nitroparaffins with Aldehydes and Ketones. J Org Chem 21(11): 1228-1231.
Cahiez et al., (2009) A new efficient catalytic system for the chemoselective cobalt-catalyzed cross-coupling of aryl Grignard reagents with primary and secondary alkyl bromides. Org Lett 11(2): 277-280.
Cueva et al., (2009) A Novel and Efficient Synthesis of Dihydrexidine. Synthesis 5: 715-720.
Fracchiolla et al., (2009) New 2-aryloxy-3-phenyl-propanoic acids as peroxisome proliferator-activated receptors alpha/gamma dual agonists with improved potency and reduced adverse effects on skeletal muscle function. J Med Chem 52 (20): 6382-6393.
Kim et al., (2001) Facile Synthesis of Phosphonium Salts Containing Carboxylic Acid Functional Group. Bull Korean Chem Soc 22(4): 351-352.
Lane et al., (2001) New design concepts for constraining glycosylated amino acids. Tetrahedron 57(30): 6531-6538.
Noboru Ono (2001) The nitro Group in Organic Synthesis. Wiley-VCH, p. 38.
Ooi et al., (2004) a concise route to (+)-lactacystin. J Org Chem 69(22): 7765-7768.
Silva et al., (2001) An expeditious synthesis of 3-nitropropionic acid and its ethyl and methyl esters. Synth Commun 31 (4): 595-600.

*Primary Examiner* — Kristin Vajda
(74) *Attorney, Agent, or Firm* — Rothwell, Figg, Ernst & Manbeck, P.C.

(57) ABSTRACT

The present invention relates to processes for the preparation of (2-Amino-2-[2-(4-octylphenyl)ethyl]propane-1,3-diol hydrochloride (Fingolimod) and pharmaceutically acceptable salts thereof, and intermediates formed in such processes.

14 Claims, No Drawings

INTERMEDIATE COMPOUNDS AND PROCESS FOR THE PREPARATION OF FINGOLIMOD

CROSS REFERENCE TO RELATED APPLICATIONS

This application is a 35 U.S.C. §371 National Phase Entry Application from PCT/IL2011/000838, filed Oct. 27, 2011, and designating the United States, which claims priority to U.S. Patent Application No. 61/407,483 filed Oct. 28, 2010, which are incorporated herein in their entireties.

FIELD OF THE INVENTION

The present invention relates to processes for the preparation of (2-amino-2-[2-(4-octylphenyl)ethyl]propane-1,3-diol (Fingolimod) and pharmaceutically acceptable salts thereof, and intermediates formed in such processes.

BACKGROUND OF THE INVENTION

Fingolimod, also known as 2-amino-2-[2-(4-octylphenyl)ethyl]-1,3-propanediol, is marketed as its hydrochloride salt, and is a sphingosine-1-phosphate receptor (S1P-R) modulator which acts as an immunomodulator by inducing lymphopenia through sequestration of circulating lymphocytes into secondary lymphoid tissues, thus preventing lymphocytes from moving into the transplanted or other affected tissues. Fingolimod (FTY720) is an innovative oral treatment for Relapsing Remitting Multiple Sclerosis (RRMS). Patients with MS display a range of symptoms that arise from demyelination in the central nervous system (CNS), which includes the brain, spinal cord and optic nerves. The destruction of the protective myelin sheath that surrounds nerve cells is thought to be due to the effects of inflammatory T cells.

The first oral S1P-R modulator to be developed, Fingolimod reduces the number of inflammatory T cells in the circulation and CNS and in so doing reduces their potential to damage nerve cells. Thus, in addition to its anti-inflammatory effects in MS, this novel therapy may have the potential to reduce neurodegeneration as well as promote endogenous repair of the CNS. Currently, no marketed treatments for MS can produce remyelination.

JP 11310556, U.S. Pat. No. 5,604,229, U.S. Pat. No. 5,952,316, US 2001/008945, US 2009/082471, WO 00/27798, WO 00/53569, WO 2005/041899, WO 2009/061374, DE 10355169, and CN1528738 disclose 2-amino-1,3-propanediol derivatives, their pharmacological activity and processes for preparing 2-amino-1,3-propanediol derivatives. The typical preparation scheme is summarized below (Scheme 1A):

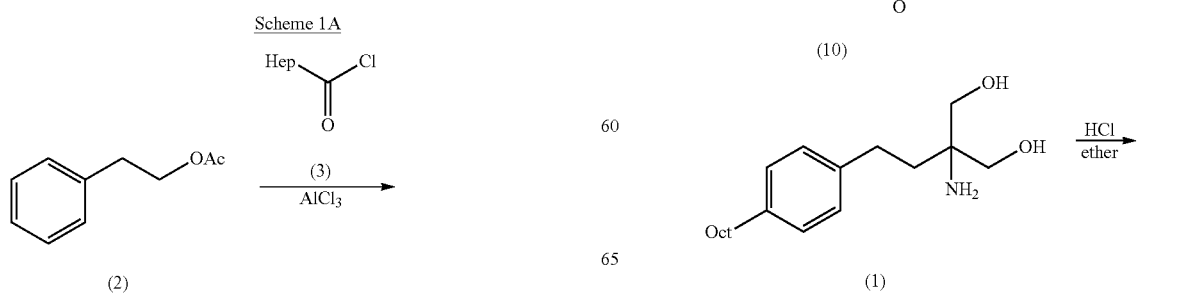

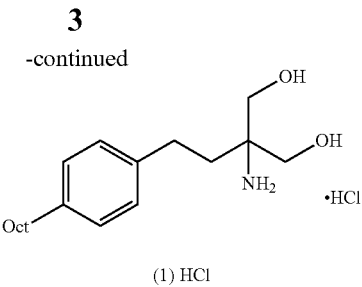

(1) HCl

However, the processes described in Scheme 1 have disadvantages in that they contain many complicated steps, and they produce intermediates as oily substances or various isomeric mixtures. Consequently, it was necessary to isolate and purify the intermediate products by conventional methods such chromatography which resulted in a complicated operation and in usage of large quantities of organic solvents.

CN1765872 discloses a process for preparing fingolimod according to Scheme 1B:

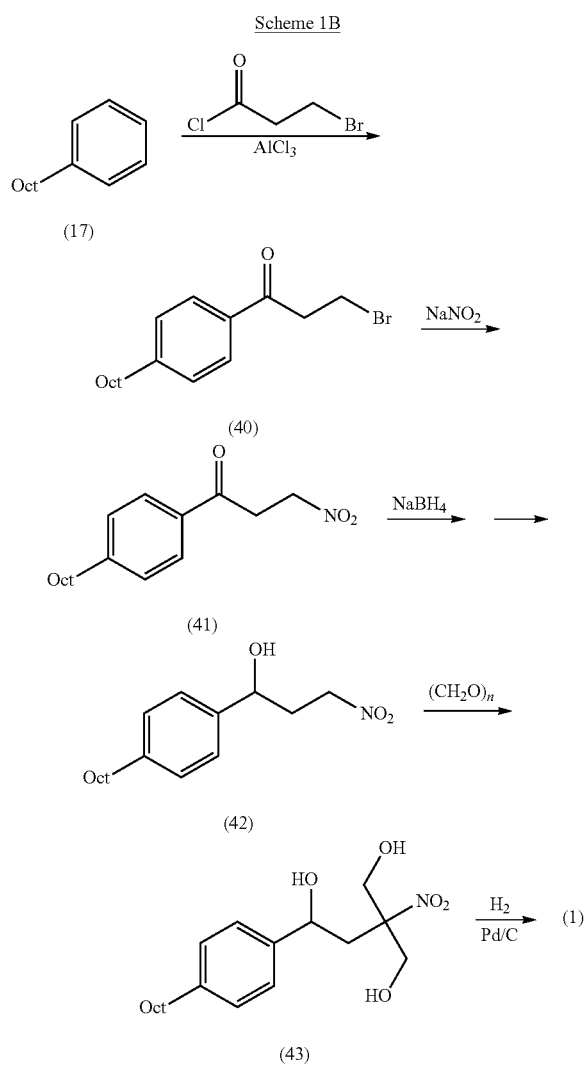

However several process stages are doubtful in terms of their implementation in view of the available literature, primarily the step of preparing 3-nitro-1-p-octylphenylpropan-1-one as a key synthon of this process by reacting 3-bromo-1-p-octylphenylpropan-1-one with sodium nitrite in DMF. According to CN1765872, the reaction proceeds at room temperature with 72% yield of 3-nitro-1-p-octylphenylpropan-1-one.

The reaction of alkyl halides with metal nitrites is an important method for the preparation of nitroalkanes. As a metal nitrite, silver nitrite (Victor-Meyer reaction), potassium nitrite, or sodium nitrite (Kornblum reaction) have been frequently used. The products are reported to be a mixture of nitroalkanes and alkyl nitrites, which are then separated by distillation or chromatography.

Scheme 1C

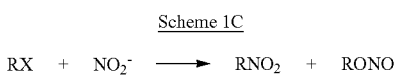

Primary and secondary alkyl iodides and bromides as well as sulfonate esters give the corresponding nitro compounds in only very modest yields upon treatment with sodium nitrite in DMF or DMSO, due mainly to the ambident character of the nitrite anion. Indeed, an efficient scalable high-yielding procedure for preparing nitroalkanes from the corresponding alkyl halides has never appeared in the literature to date. For example, reaction of 4-(3-bromopropyl)-1,2-dimethoxybenzene with sodium nitrite in DMF at room temperature (utilizing the same reaction conditions taught by CN1765872) gave the desired nitroalkane in 54% yield only by halting the reaction at the point where nitrite ester formation was minimal and did not significantly affect the nitrosation of 1,2-dimethoxy-4-(3-nitropropyl)benzene into its corresponding nitrolic acid. Although significant amounts of starting material could be recovered, it was found that chromatographic separation of the resulting mixture was an unavoidable necessity. Other practical problems associated with the teachings of CN1765872 are the formation of 3-nitro-1-(p-octylphenyl)propan-1-ol as an oil which is difficult to operate in the production stage, moderate yields of formylation (56%) and hydrogenation (66%) steps and low overall yield (~20%).

Therefore, there exists a need to develop a process for obtaining Fingolimod which is cost effective, is based on available reagents, is scalable with ease and is industrially feasible. We herein disclose such a process.

SUMMARY OF THE INVENTION

The present invention provides several processes for preparing Fingolimod, and certain novel intermediates formed in said processes.

In one embodiment, the present invention provides a process for preparing Fingolimod or pharmaceutically acceptable salts thereof, which is designated herein "Process 1" and illustrated in Scheme 2 hereinbelow. The process comprises the steps of:

a) reacting octylbenzene with a 3-nitropropanoic acid derivative of formula A:

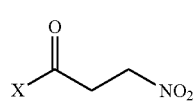

wherein X is a halogen, preferably Cl, or an anhydride, so as to obtain 3-nitro-1-(4-octylphenyl)propan-1-one of formula (12)

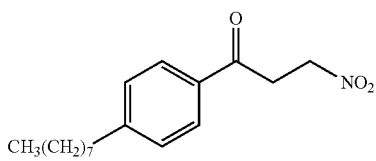

(12)

b) reducing 3-nitro-1-(4-octylphenyl)propan-1-one (12) with a reducing agent to obtain 3-nitro-1-(4-octylphenyl)propan-1-ol;

c) protecting the hydroxyl group of 3-nitro-1-(4-octylphenyl)propan-1-ol so as to obtain compound (13A):

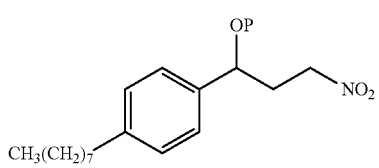

(13A)

wherein P is a hydroxyl protecting group;

d) bis-hydroxymethylation of compound (13A) with formaldehyde or an equivalent thereof in the presence of catalyst, and removal of the hydroxyl protecting group to obtain compound (14):

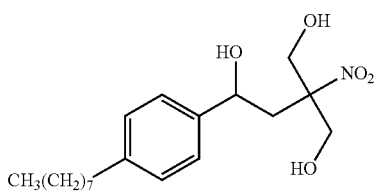

(14)

e) reducing compound (14) to Fingolimod (1); and f) optionally, converting Fingolimod (1) to a pharmaceutically acceptable salt thereof.

In some embodiments, step (a) is conducted in the presence of a Friedel-Crafts catalyst (e.g., $AlCl_3$, $FeCl_3$, $SnCl_4$, $TiCl_4$, $ZnCl_2$ or $BF_3$). In other embodiments, step (a) is conducted in the presence of a metal salt of an organic acid (e.g., a metal triflate, preferably hafnium triflate or cerium triflate). In other embodiments, step (a) is conducted in the presence of a protic acid (e.g. HF, $H_2SO_4$, $CF_3SO_3H$ and an ion-exchange resin, preferably Nafion or zeolite). Each possibility represents a separate embodiment of the present invention.

In some embodiments, the reducing agent in step (b) is $NaBH_4$. Other reducing agents that can be used for this step include other complex hydride reducing reagents such as lithium, calcium or zinc borohydrides or lithium aluminum hydride and the like. Each possibility represents a separate embodiment of the present invention.

The hydroxy protecting group P can be any hydroxyl protecting group known in the art. A currently preferred hydroxyl protecting group is acetyl ($COCH_3$).

In some embodiments, step (c), i.e., the protection of 3-nitro-1-(4-octylphenyl)propan-1-ol is carried out by acylation with acetyl chloride or acetic anhydride in the presence of base. Advantageously, the reduction of 3-nitro-1-(4-octylphenyl)propan-1-one (12) to 3-nitro-1-(4-octylphenyl)propan-1-ol and its protection (e.g., acylation) to compound (13A) can be carried out in one step, without isolation of the intermediate having a free hydroxyl.

In some embodiments, the bis-hydroxymethylation of compound (13A) (step d) is carried out using a formaldehyde derivative of formula $(CH_2)_nO$ which may be, e.g., formaldehyde, paraformaldehyde or trioxane. In some embodiments, this reaction is conducted in the presence of a base. In other embodiments, the bis-hydroxymethylation of compound (13A) and deprotection to compound (14) is carried out in one step. Each possibility represents a separate embodiment of the present invention.

In some embodiments, the reduction step (e) comprises hydrogenating compound (14) to Fingolimod (1) in the presence of catalyst. In particular embodiments, the hydrogenation step is carried out in the presence of Pd/C as a catalyst.

Certain intermediates formed during this process are novel and represent further aspects of the present invention. Thus, in one embodiment, the present invention further relates to a protected derivative of formula (13A) as described herein or, more generally, to compound represented by the following structure:

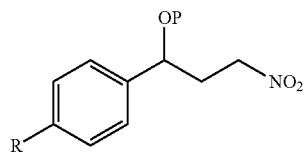

wherein P is a hydroxyl protecting group and R is an alkyl. In one embodiment, P is acetyl ($COCH_3$). In another embodiment, R is octyl. In yet another embodiment, P is acetyl ($COCH_3$) and R is octyl. Each possibility represents a separate embodiment of the present invention.

In another embodiment, the present invention relates to an intermediate of formula (14) or, more generally, a compound represented by the following structure:

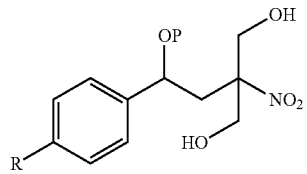

wherein P is a hydroxyl protecting group and R is an alkyl. In another embodiment, R is octyl. In yet another embodiment, P is acetyl ($COCH_3$). In another embodiment, P is acetyl ($COCH_3$) and R is octyl. Each possibility represents a separate embodiment of the present invention.

Alternatively, in an another embodiment, the present invention provides a process for preparing Fingolimod or pharmaceutically acceptable salts thereof, which is designated herein "Process 2" and illustrated in Scheme 3 hereinbelow. The process can be conducted in accordance with alternative embodiments, designated herein "Process 2A" and "Process 2B". Process 2A comprises the steps of a) reacting 3-nitropropylbenzene with an octanoic acid derivative of formula B:

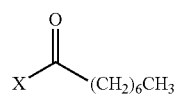

wherein X is a halogen, preferably Cl, or an anhydride so as to generate 1-(4-(3-nitropropyl)phenyl)nonan-1-one of formula (17);

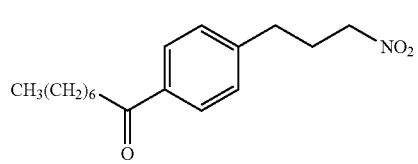

b) bis-hydroxymethylation of compound (17) with formaldehyde or an equivalent thereof in the presence of a catalyst to generate a compound of formula (18):

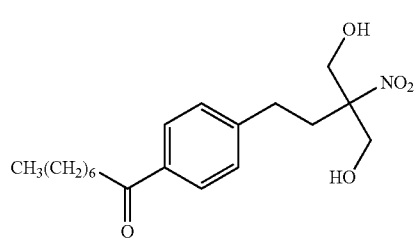

c) reducing compound (18) to Fingolimod (1); and
d) optionally, converting Fingolimod (1) to a pharmaceutically acceptable salt thereof.

Process 2B, which is also illustrated in Scheme 3 hereinbelow, comprises the steps of:
a) bis-hydroxymethylation of 3-nitropropylbenzene with formaldehyde or an equivalent thereof in the presence of a catalyst to generate a compound of formula (19):

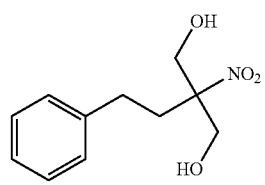

b) converting compound (19) to an acetal or ketal represented by the structure of formula (20A):

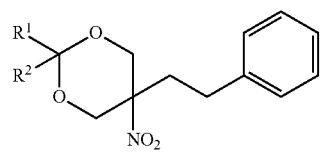

wherein $R^1$ and $R^2$ are each independently H, an alkyl or an aryl;

c) reacting compound (20A) with an octanoic acid derivative of formula B

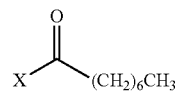

wherein X is a halogen, preferably Cl, or an anhydride so as to generate a compound of formula (21A):

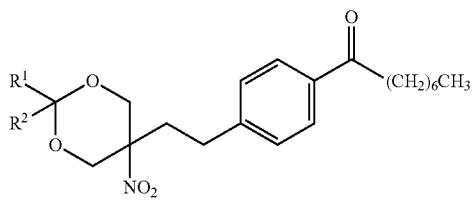

d) reducing compound (21A) followed by removal of the acetal or ketal group so as to obtain to Fingolimod (1); and
e) optionally, converting Fingolimod (1) to a pharmaceutically acceptable salt thereof.

The steps of reacting compound (16) (3-nitropropylbenzene) or (20A) with an octanoic acid derivative can be carried out in the presence of a Friedel-Crafts catalyst, a metal salt of an organic acid, or a protic acid, using the same or similar conditions to those described above for Process 1.

Furthermore, the bis-hydroxymethylation of compound (17) or compound (19) can be carried out with a formaldehyde derivative of formula $(CH_2)_nO$, e.g., formaldehyde, paraformaldehyde or trioxane, preferably in the presence of a base, using the same or similar conditions to those described above for Process 1.

In some embodiments, $R^1$ and $R^2$ in compounds (20A) or (21A) are each $CH_3$.

Certain intermediates formed during this process are novel and represent further aspects of the present invention. Thus, in one embodiment, the present invention further relates to a compound of formula (17), i.e., a compound represented by the following structure:

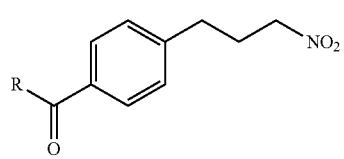

wherein R is heptyl.

In other embodiments, the present invention relates to a compound represented by formula (20A) or (21A) or, more specifically, to a compound represented by the following structure:

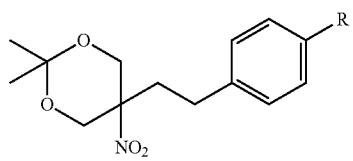

wherein R is selected from H, $CH_3(CH_2)_6C(O)-$ and $CH_3(CH_2)_7-$.

Alternatively, in another embodiment, Fingolimod can be prepared by yet a different method, based on Wittig or Horner-Wadsworth-Emmons reactions using cheap and available tris(hydroxymethyl)aminomethane (TRIS) as starting material. This process, designated herein as "Process 3" and illustrated in Scheme 4 hereinbelow, comprises the following steps:

a) reacting an aldehyde of formula (24A)

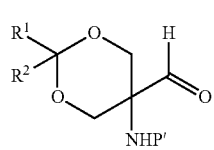
(24A)

with a Wittig reagent of formula (23A) or a phosphonate of formula (25A);

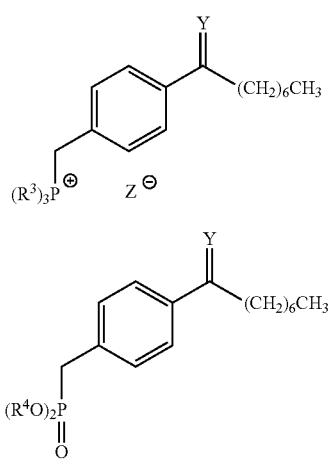

wherein

Y is O or $H_2$ (i.e., C=Y together represent a methylene ($CH_2$) group);

$R^1$ and $R^2$ are each independently H, an alkyl or an aryl;

$R^3$ and $R^4$ are each independently alkyl or aryl;

P' is a nitrogen protecting group; and

Z is a counter-ion, preferably a halogen;

in the presence of a base so as to obtain a compound of formula (26A):

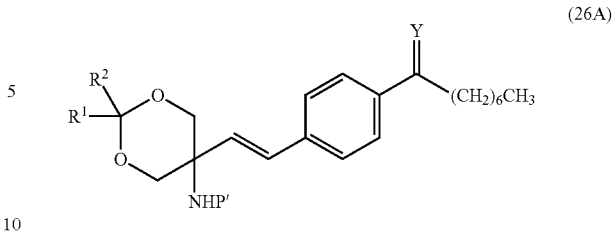
(26A)

wherein $R^1$, $R^2$, Y and P' are as described above, b) reducing compound (26A) to generate compound (27A):

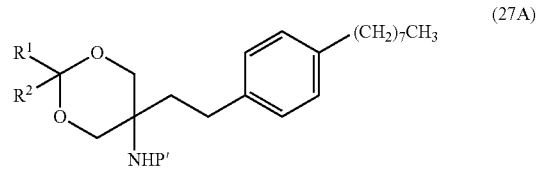
(27A)

followed by removal of the acetal or ketal and nitrogen protecting group so as to obtain Fingolimod (1); and c) optionally, converting Fingolimod (1) to a pharmaceutically acceptable salt thereof.

In some embodiments, the reducing step (b) is carried out by hydrogenating compound (26A) in the presence of a catalyst, for example Pd/C. Furthermore, the nitrogen protecting group P' can be any protecting group known in the art, for example Boc.

In one embodiment, Process 3 comprises the following steps, as summarized in Scheme 4A hereinbelow:

a) reacting an aldehyde of formula (24)

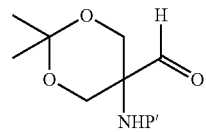
(24)

with a Wittig reagent of formula (23) or a phosphonate of formula (25)

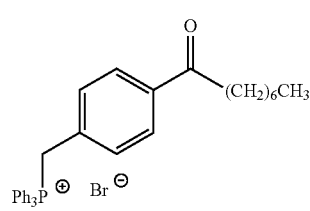
(23)

-continued

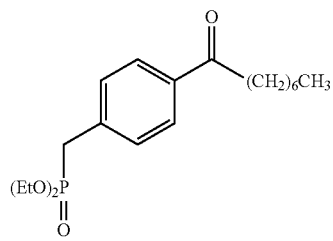
(25)

in the presence of a base so as to obtain a compound of formula (26)

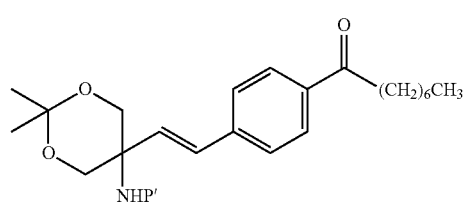
(26)

wherein P' is as defined above;

b) reducing compound (26) to generate compound (27):

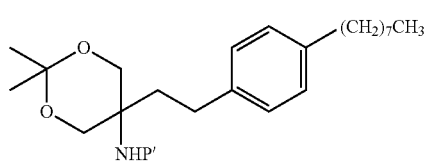
(27)

followed by removal of the ketal and nitrogen protecting group so as to obtain Fingolimod (1); and c) optionally, converting Fingolimod (1) to a pharmaceutically acceptable salt thereof.

Certain intermediates formed during this process are novel and represent further aspects of the present invention. Thus, in one embodiment, the present invention further relates to a compound of formula (26A) or (27A) i.e., a compound represented by the following structure:

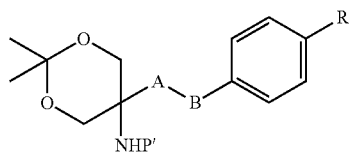

wherein P' is a nitrogen protecting group such as Boc; and either A-B is CH=CH, and R=CH$_3$(CH$_2$)$_6$C(O)—; or A-B is CH$_2$—CH$_2$, and R is CH$_3$(CH$_2$)$_7$—.

In another embodiment, the present invention relates to an intermediate of formula (23A) or (25A):

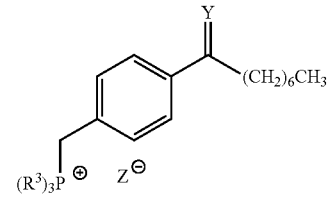
(23A)

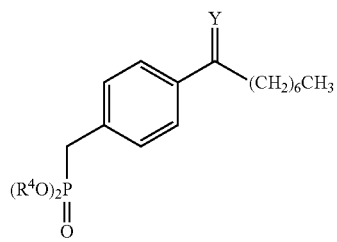
(25A)

wherein
Y is O or H$_2$;
R$^3$ and R$^4$ are each independently alkyl or aryl; and
Z is a counter-ion, preferably a halogen.

In one embodiment, R$^3$ is phenyl, R$^4$ is ethyl, and Z is a halogen, preferably a bromine.

If desired, Fingolimod prepared by any of the Processes 1, 2 or 3 can further be converted into its pharmaceutically acceptable salt, such as the hydrochloride salt, in a manner known to a person of skill in the art.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The applicants have found several new processes, by which the Fingolimod may be prepared on a manufacturing scale from commercially available starting materials. These processes are designated herein "Process 1", "Process 2", and "Process 3".

Chemical Definitions:

An "alkyl" group refers to any saturated aliphatic hydrocarbon, including straight-chain, and branched-chain. In one embodiment, the alkyl group has 1-12 carbons designated here as C$_1$-C$_{12}$-alkyl. In another embodiment, the alkyl group has 1-6 carbons designated here as C$_1$-C$_6$-alkyl. In another embodiment, the alkyl group has 1-4 carbons designated here as C$_1$-C$_4$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl. Each possibility represents a separate embodiment of the present invention.

An "aryl" group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. Each possibility represents a separate embodiment of the present invention.

Process 1:

In one embodiment, the present invention provides a process for preparing Fingolimod or pharmaceutically acceptable salts thereof, designated herein as "Process 1", as illustrated in Scheme 2:

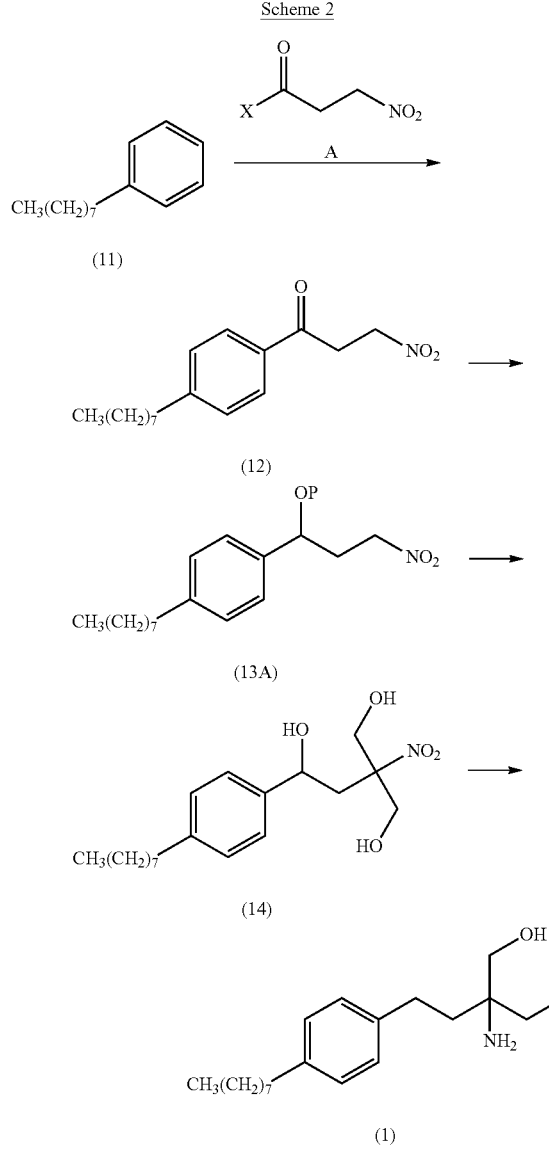

One non-limiting embodiment of Process 1 is illustrated in Scheme 2A:

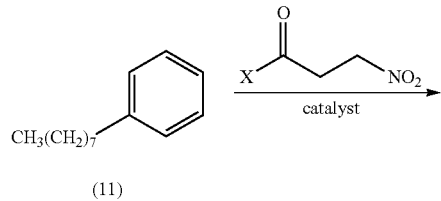

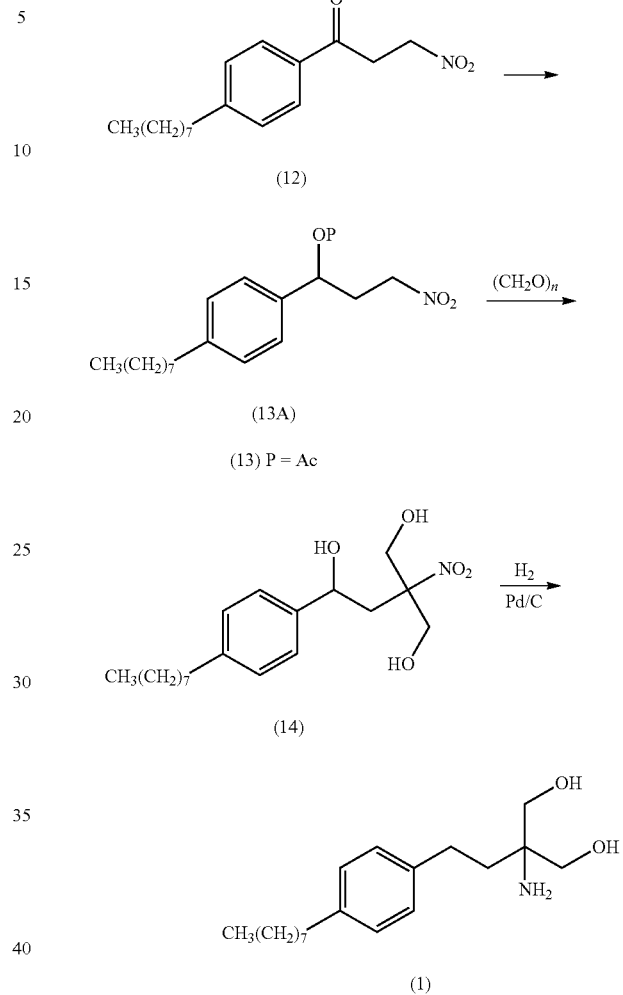

In accordance with this non-limiting embodiment of Process 1, Fingolimod can be prepared from a compound of formula (11) by several steps, as illustrated in Scheme 2 or 2A, and in the experimental section.

The process comprises the following steps:

a) reacting octylbenzene with a 3-nitropropanoic acid derivative of formula A wherein X is a halogen, preferably Cl, or an anhydride, so as to obtain 3-nitro-1-(4-octylphenyl)propan-1-one of formula (12);

b) reducing 3-nitro-1-(4-octylphenyl)propan-1-one (12) to 3-nitro-1-(4-octylphenyl)propan-1-ol with a reducing agent;

c) protecting the hydroxyl group of 3-nitro-1-(4-octylphenyl) propan-1-ol so as to obtain compound (13A) wherein P is a hydroxyl protecting group;

d) bis-hydroxymethylation of compound (13A) with formaldehyde or an equivalent thereof in the presence of catalyst, and removal of the hydroxyl protecting group to obtain compound (14);

e) reducing compound (14) to Fingolimod (1); and f) optionally, converting Fingolimod (1) to a pharmaceutically acceptable salt thereof.

Octylbenzene (11), which is used here as a raw material is a commercially-available reagent, or it can be produced by well-known methods described in Org. Lett., 2009, Vol. 11, No. 2, p. 277 or WO 2009/133045, the contents of each of which are incorporated by reference herein.

Step (a) of this process comprises converting octyl benzene into a Fingolimod intermediate 3-nitro-1-(4-octylphenyl) propan-1-one (12), by reacting octylbenzene with a 3-nitro-propanoic acid derivative (e.g., anhydride (Xα—OC(=O)R wherein R is alkyl, aryl etc.) or halo wherein halo is selected from F, Cl, Br or I) in the presence of a catalyst. It should be mentioned that the direct conversion of compound (11) to (12) with a 3-nitropropanoic acid derivative is advantageous over prior art methods which involve coupling of octylbenzene with a halo propionic acid derivative to generate a halo intermediate followed by reaction with a metal nitrite, which methods have various drawbacks as outlined above. The process described herein is conducted in one step, is economically more attractive because it uses commercially available materials and only one solvent (which can be recycled), and it avoids the use of hazardous materials such as nitrites.

The reaction may be carried out in the presence of a Friedel-Crafts catalyst, such as $AlCl_3$, $FeCl_3$, $SnCl_4$, $TiCl_4$, $ZnCl_2$, $BF_3$, and like; metal salts of organic acids, such as metal triflates (hafnium triflate, cerium triflate, and like) or of protic acids (for example, HF, $H_2SO_4$, $CF_3SO_3H$), ion-exchange resins, such as Nafion, zeolite and the like. Each possibility represents a separate embodiment of the present invention.

The acylation reaction is conducted in any solvent suitable for the Friedel-Crafts reaction, such as but not limited to methylene chloride, chloroform, dichloroethane, dioxane, nitroalkanes or their mixtures. The reaction can be performed in the presence of additives, such as $AgSbF_6$, $AgBF_6$, preferably, $LiClO_4$. Each possibility represents a separate embodiment of the present invention.

The reaction can further be accelerated by using ionic liquids as a solvent and under microwave irradiation. The reaction can be carried out at any temperature between about 0° C. and about 120° C., for example at room temperature or at reflux temperature which will vary depending on the solvent being used.

Compound (12) is pure enough for the use on the next step, but if necessary, it can be further purified by any suitable technique, for example, by distillation or by column chromatography.

In the next step of the process, a Fingolimod intermediate (13A) is prepared by reduction of compound (12) with a reducing agent, followed by protecting the hydroxyl group (e.g., by acylation). The reducing agent can be, for example borane and its complexes with dimethylsulfide, pyridine, triethylamine and like; lithium and sodium borohydride in presence of a Lewis acid, such as boron trifluoride diethyl ether complex, aluminum-; titanium- or cobalt-chlorides and the like, or in the presence of trimethylchlorosilane or phosphorus oxychloride; or an aluminum hydride such as $AlH_3$ and its complex with amines, $LiAlH_4$, sodium bis(2-methoxyethoxy)aluminum hydride (Red-Al) or diisobutylaluminum hydride. Preferably, the reducing agent is sodium borohydride. Each possibility represents a separate embodiment of the present invention.

The intermediate compound 3-nitro-1-(4-octylphenyl)propan-1-ol, formed by the aforementioned reduction step, may undergo dehydration (under heating or acidic catalyst assistance) to form the undesirable 3-(nitroprop-1-enyl)-4-octylbenzene, which may be subject to isomerization, decomposition or polymerization, all undesired reactions (analogous reactions are described in Noboru Ono, The nitro Group in Organic Synthesis. Wiley-VCH, 2001, p. 38).

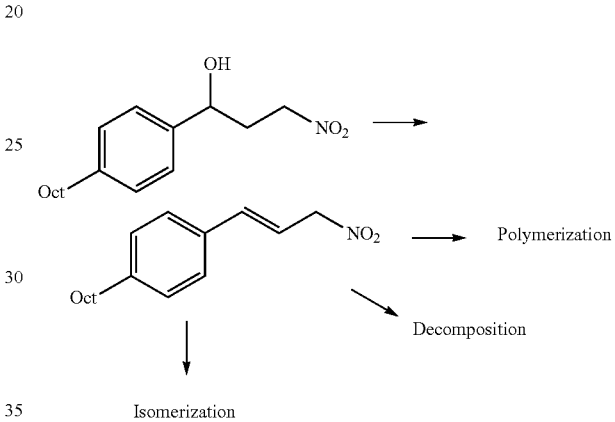

wherein Oct=octyl.

Because of this, the handling of this compound demands special precautions and the compound cannot be stored for a long time under ambient conditions, as is sometimes required during manufacturing processes. In addition, 3-nitro-1-(p-octylphenyl)propan-1-ol is difficult to purify (only by chromatography), because it cannot be distilled or crystallized easily.

To overcome such problems and to increase the stability of the intermediate, the hydroxyl group of this 3-nitro-1-(4-octylphenyl)propan-1-ol intermediate can be protected by a protecting group to generate compound (13A). Suitable hydroxyl protecting groups include, but are not limited to, triorganosilyl, such as trimethylsilyl (TMS), triethylsilyl (TES), t-butyldimethylsilyl (TBDMS), t-butyldiphenylsilyl (TBDPS), tripropylsilyl, triisopropylsilyl, triphenylsilyl, and the like, methoxymethyl, benzyloxymethyl, methoxyethoxymethyl, 2-(trimethylsilyl)ethoxymethyl, tetrahydropyranyl, t-butyl, 4-methoxybenzyl and analogous groups. Each possibility represents a separate embodiment of the present invention.

One preferred hydroxyl protecting group is acyl, more preferably, acetyl (COCH$_3$), which can be attached to the hydroxyl of the 3-nitro-1-(4-octylphenyl)propan-1-ol by a reaction with acyl anhydride, such as acetyl anhydride, or acetyl halide, such as acetyl chloride, in the presence of a base. Examples of the bases include, but are not limited to, organic bases such as pyridine, triethylamine, sodium alkoxide or potassium alkoxide and the like or inorganic base such as sodium carbonate, potassium carbonate, sodium or potassium hydroxide and the like. The protection of the hydroxyl group provides a stable intermediate, for crystallization and transferred without decomposition. Each possibility represents a separate embodiment of the present invention.

Other suitable hydroxyl protecting groups and hydroxyl protecting group reagents are disclosed in Greene. Protective Groups in Organic Synthesis, 2nd ed, John Wiley & Sons, New York, 1991, the contents of which are incorporated by reference herein.

Next, a Fingolimod intermediate of formula (14), is prepared by reacting 1-substituted phenyl-3-nitro-propan-1-ol (13) or more generally (13A) with hydroxymethylation reagent (CH$_2$)$_n$O, such as formaldehyde in an organic solvent or in water (formalin), paraformaldehyde or trioxane. The reaction may be carried out in a solvent in the presence of base. Preferably, the reaction is carried out at a temperature between about −10° C. and about 50° C., more preferably at about 20-25° C. The reaction is conducted in any suitable solvent, which may be for example selected from the group consisting of C1 to C5 alcohols, C2 to C7 esters, C4 to C7 ethers, C1 to C5 carboxylic acid amides, water, or suitable mixtures of these solvents. Preferred solvents are alcohols, such as methanol, ethanol, isopropanol, water or their mixtures. Examples of the bases include but not limited to alkali metal hydroxides, carbonates, bicarbonates and alkoxides, such as potassium bicarbonate, sodium bicarbonate, potassium carbonate, sodium carbonate, sodium hydroxide, potassium hydroxide, calcium hydroxide, and the like; amines such as triethylamine, diisopropylethylamine, N-methylmorpholine, pyridine, lutidine DBU, DBN, tetramethylguanidine (TMG), P(RNCH$_2$CH$_2$)$_3$N (PAP), and like; KF, n-Bu$_4$NF, Al$_2$O$_3$—KF, basic resins such as amberlyst A-21, amberlite IRA-420. Each possibility represents a separate embodiment of the present invention.

In one embodiment, the base is a solid base, such as Amberlyst. The use of a solid base may increase reaction yields, and makes work-up and recycling of the base more technologically and economically suitable.

The reaction may be carried out in water using the above-mentioned bases and phase transfer catalysts, for example, NaOH and cetyltrimethylammonium chloride (CTACl). After reaction completion, the protecting group can be removed by methods described in Greene. Protective Groups in Organic Synthesis, 2nd ed, John Wiley & Sons, New York, 1991, the contents of which are incorporated by reference. The preferred acetyl protecting group can be removed under basic conditions at a temperature between about 30° C. and about 70° C., more preferably at about 40-50° C.

The preparation of compound (14) may be carried out in one stage, by performing the reaction of 1-substituted phenyl-3-nitro-propan-1-ol (13) with formaldehyde at about 20-25° C. and then deprotecting of hydroxyl group at about 40-50° C., using the same solvent and base without separation and purification of the intermediate compound.

Finally, Fingolimod is prepared by reduction of compound (14) with a reducing agent, preferably in an organic solvent and/or water. Examples of the reducing agent to be used for the reduction of compound (14) include metal hydrides, such as lithium aluminum hydride, hydrogen (H$_2$) in the presence of a transition metal such as palladium, rhodium or ruthenium-based reagents, for example, Pd/C, platinum oxide, and like; Raney nickel; and metals such as iron, zinc or tin in acidic or basic media. The reduction of compound (14) to compound (1) comprises two parts: reduction of the hydroxyl group and reduction of the nitro group. The reduction of both groups can be carried out in one step using the same reducing agent (e.g., by hydrogenation using H$_2$ in the presence of a catalyst). Alternatively, each reduction step can be carried out separately in any order, using the same or different reducing agents, with or without isolation of reaction intermediates. Each possibility represents a separate embodiment of the present invention.

Examples of the solvents to be used for the reduction of compound (14) include, but are not limited to, water, methanol, ethanol, tert-butyl alcohol, tetrahydrofuran, diethyl ether, dioxane, acetone, ethyl acetate, acetic acid, benzene, toluene, xylene, dimethylformamide and dimethyl sulfoxide and their mixtures.

The reduction of compound (14) generally proceeds at a temperature in the range of about 0° C. to about 70° C., but a temperature lower or higher than this temperature range may be selected on demand. The hydrogenation may be carried out at about 1 to 30 about atm of hydrogen pressure.

The thus prepared Fingolimod can be transformed in its pharmaceutical salts (e.g., the hydrochloride salt) by methods described in literature, for example EP 0989113, U.S. Pat. No. 6,284,915; and WO 99/01419, the contents of each of which is incorporated by reference herein.

Process 2:

Alternatively, Fingolimod can be prepared from (3-nitropropyl)benzene by acylation with octanoyl chloride, hydroxymethylation and reduction ("Process 2A": 16→17→18→1 in Scheme 3) or hydroxymethylation, protection, acylation and reduction (Process 2B: 16→19→20A→21A→1 in Scheme 3). These alternative processes comprise the following steps:

Process 2A:

a) reacting 3-nitropropylbenzene with an octanoic acid derivative of formula B wherein X is a halogen, (e.g., Cl, F, Br or I), preferably Cl, or an anhydride so as to generate 1-(4-(3-nitropropyl)phenyl)nonan-1-one of formula (17);

b) bis-hydroxymethylation of compound (17) with formaldehyde or an equivalent thereof in the presence of a catalyst to generate a compound of formula (18);
c) reducing compound (18) to Fingolimod (1); and
d) optionally, converting Fingolimod (1) to a pharmaceutically acceptable salt thereof.

Process 2B:
a) bis-hydroxymethylation of 3-nitropropylbenzene with formaldehyde or an equivalent thereof in the presence of catalyst to generate a compound of formula (19);
b) converting compound (19) to an acetal or ketal represented by the structure of formula (20A) wherein $R^1$ and $R^2$ are each independently H, an alkyl or an aryl;
c) reacting compound (20A) with an octanoic acid derivative of formula B wherein X is a halogen, e.g., Cl, F, Br or I, preferably Cl, or an anhydride so as to generate a compound of formula (21A);
d) reducing compound (21A) followed by removal of the acetal or ketal group so as to obtain to Fingolimod (1); and
e) optionally, converting Fingolimod (1) to a pharmaceutically acceptable salt thereof.

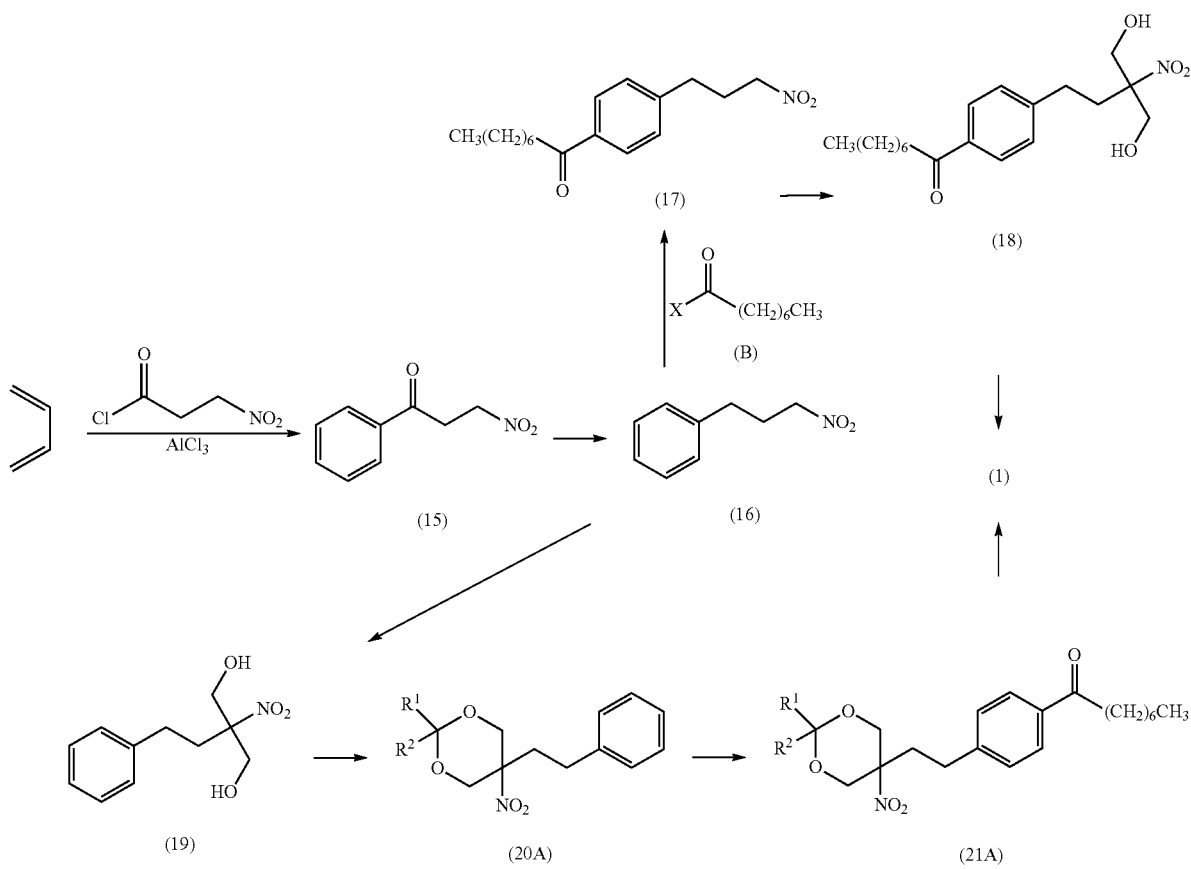

Scheme 3

The process steps (acylation, hydroxymethylation, reduction) may be carried out under the similar conditions to those described for the reactions presented for Process 1 (Scheme 2). One particular and non-limiting embodiment of Process 2 is illustrated in Scheme 3A:

Scheme 3A

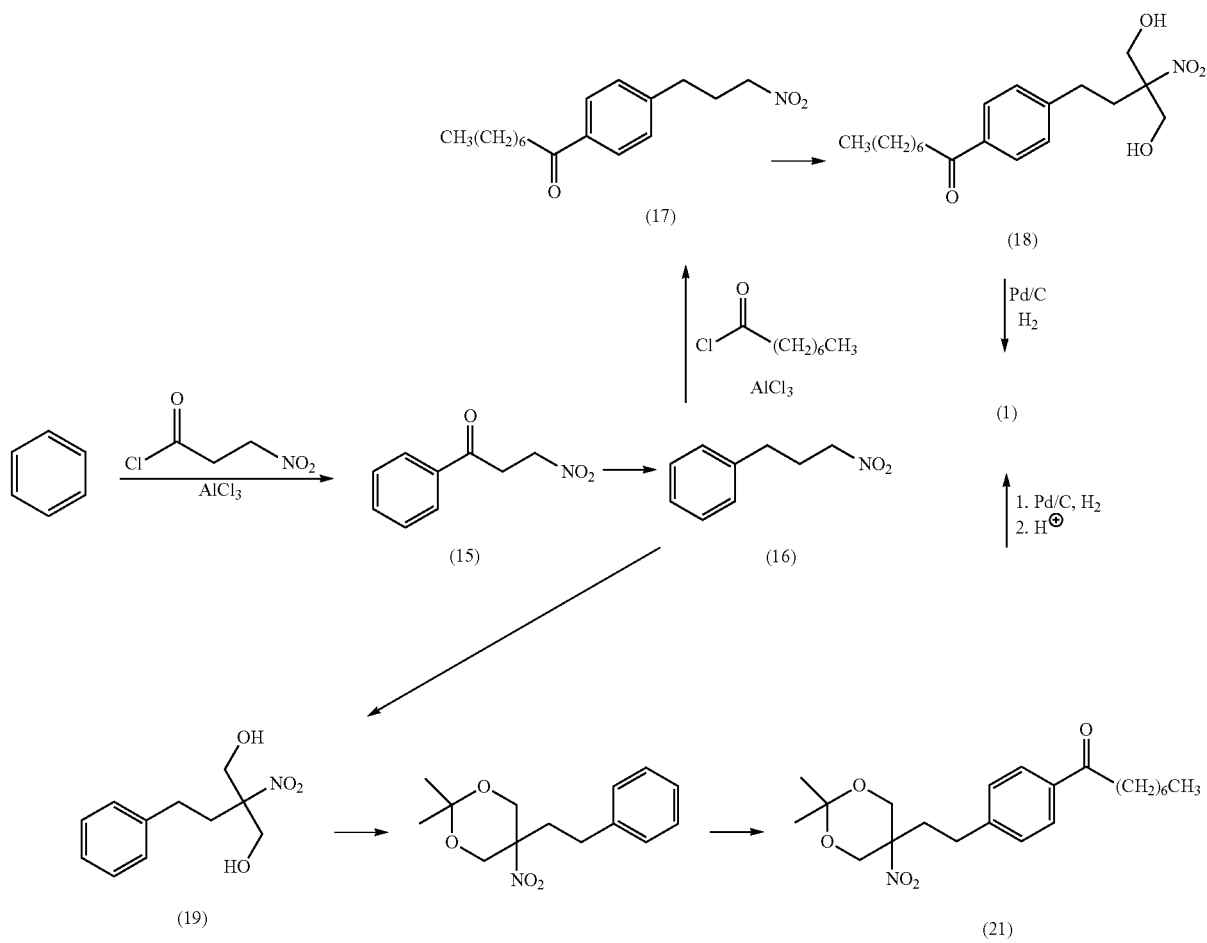

Process 3

Alternatively, Fingolimod can be prepared from tris(hydroxymethyl)aminomethane (TRIS), a cheap and commercially-available starting material using Wittig or Horner-Wadsworth-Emmons reactions, as illustrated in Scheme 4. The process comprises the following steps:

a) reacting an aldehyde of formula (24A) with a Wittig reagent of formula (23A) or a phosphonate of formula (25A), wherein Y is O or $H_2$ (i.e., C=Y represents a $CH_2$ (methylene) group); $R^1$ and $R^2$ are each independently H, an alkyl or an aryl; $R^3$ and $R^4$ are each independently alkyl or aryl; P' is a nitrogen protecting group; and Z is a counter-ion, preferably a halogen; in the presence of a base so as to obtain a compound of formula (26A), b) reducing compound (26A) to obtain a compound of formula (27A) followed by removal of the acetal or ketal and nitrogen protecting group so as to obtain Fingolimod (1); and c) optionally, converting Fingolimod (1) to a pharmaceutically acceptable salt thereof.

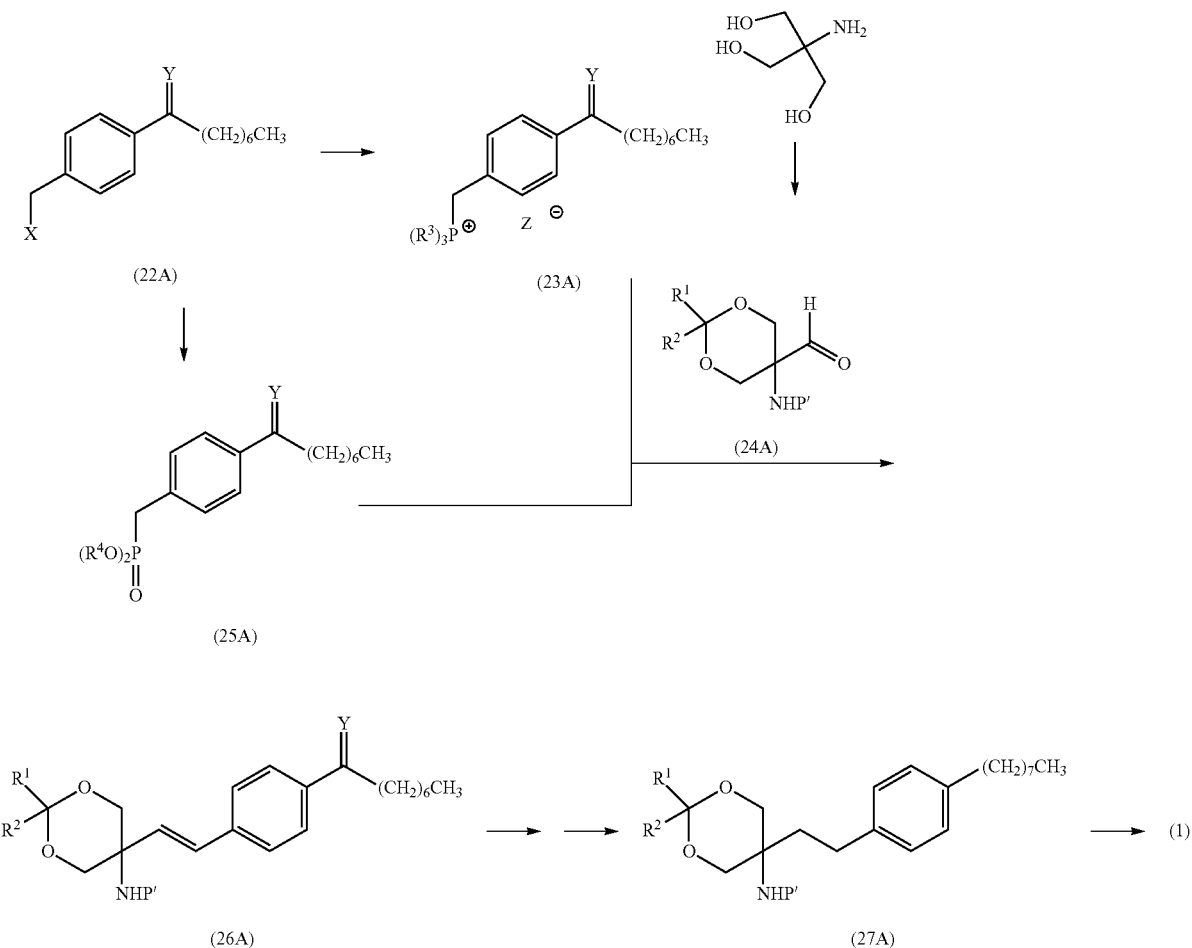

Scheme 4

Scheme 4, Z is a counter-ion, which is preferably a halogen (e.g., F, Cl, Br or I). Other suitable counter-ions include, but are not limited to, sulfonates, trifluoroacetates [*Bull. Korean Chem. Soc.* 2001, Vol. 22, No. 4 351] and the like.

In one embodiment Y is O. In another embodiment, Y is $H_2$, i.e., Y together with the carbon to which it is attached forms a methylene ($CH_2$) group. Each possibility represents a separate embodiment of the present invention.

One particular and non-limiting embodiment of Process 3 is illustrated in Scheme 4A. The process comprises the following steps:

a) reacting an aldehyde of formula (24) with a Wittig reagent of formula (23) or a phosphonate of formula (25), in the presence of a base so as to obtain a compound of formula (26);

b) reducing compound (26) so as to generate compound (27) followed by removal of the ketal and nitrogen protecting group so as to obtain Fingolimod (1); and c) optionally, converting Fingolimod (1) to a pharmaceutically acceptable salt thereof.

Scheme 4A

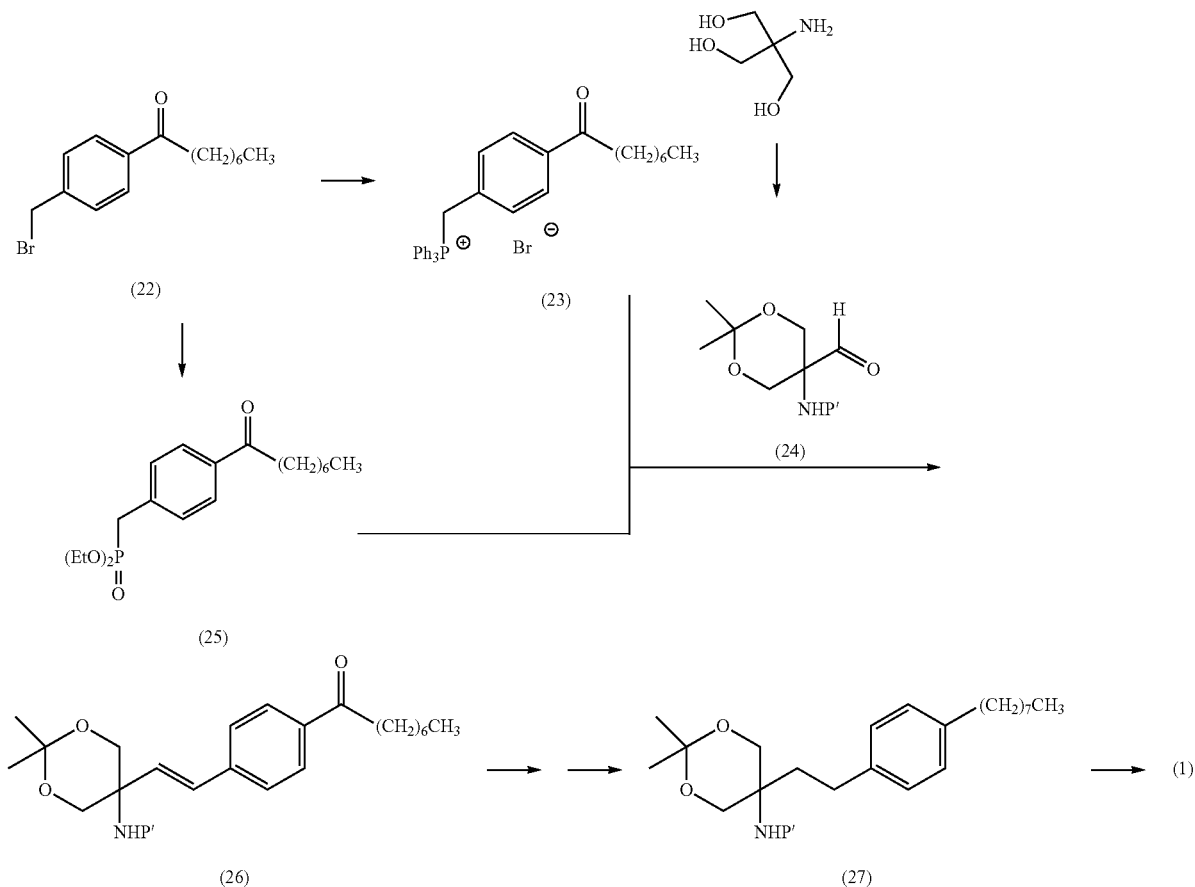

The protecting group P' can be any nitrogen protecting groups, for example carbamates, amides, N-benzyl derivatives, and imine derivatives. Non-limiting examples of nitrogen-protecting groups are acetyl ($COCH_3$), benzoyl, benzyl, benzyloxycarbonyl (Cbz), formyl, phenylsulfonyl, pivaloyl, tert-butoxycarbonyl (Boc), tert-butylacetyl, and triphenylmethyl (trityl), fluorenylmethyloxycarbonyl (Fmoc), p-nitrobenzenesulfoethoxycarbonyl propargyloxycarbonyl, picolinyl, prenyl, o-nitrobenzyloxy methyl, 4-methyoxyphenoxymethyl, guaiacolmethyl, siloxymethyl, such as triisopropylsiloxymethyl, 2-cyanoethyoxymethyl, 2-quinolinylmethyl, dichloroacetyl, trichloroacetyl, 2-[4-nitrophenyl] ethylsulfonate and the like. Other suitable nitrogen protecting groups and nitrogen protecting group reagents are disclosed in Greene. Protective Groups in Organic Synthesis, 2nd ed, John Wiley & Sons, New York, 1991, the contents of which are incorporated by reference herein.

Tris(hydroxymethyl)aminomethane (TRIS) may be converted to compound (24A) by known methods, for example Tetrahedron, 2001, 57, p. 6531. The preparation of two phosphorus containing precursors (23A) and (25A) may be achieved by methods described for their analogous compounds (Organophosphorus Reagents: A Practical Approach In Chemistry, P. J. Murphy, Oxford University Press, USA, 2004, 288 pp; Organophosphorus reagents in organic synthesis, ed. J. I. G. Cadogan, Academic Press, London; New York: 1979, 608 pp.), using the bromo derivative (22) as a starting material (U.S. Pat. No. 5,604,229) or, more generally, a compound of formula (22A), wherein X is a leaving group, such as a halogen or sulfonate. The contents of each of these references are incorporated by reference herein. In a particular embodiment, $R^1$ and $R^2$ are each methyl, and the compound of formula (24A) is represented by the structure of compound (24). Also, particular embodiments of compound (23A) and (25A) are represented by the structures (23) or (25), respectively (Scheme 4A).

Next, a Fingolimod intermediate of formula (26A) is prepared by a reaction of a Wittig reagent (23A) or phosphonate (25A) with aldehyde (24A) in the presence of a base in an appropriate solvent. In a particular embodiment, a Fingolimod intermediate of formula (26), is prepared by a reaction of a Wittig reagent (23) or phosphonate (25) with aldehyde (24) (Scheme 4A). Examples of solvents for this reaction include, but are not limited to ethers (diethyl, diisopropyl, tert-butyl methyl ether, tetrahydrofuran, dioxane), acetonitrile, toluene, propionitrile, N,N-dimethylformamide, dimethylsulphoxide, N-methylpyrrolidone. Of these, polar solvent are currently preferred, with THF-DMF mixture being preferred currently preferred example.

Suitable bases for this reaction include, but are not limited to, alkali metal and alkaline earth carbonates, hydroxides and alkoxides, for example potassium bicarbonate, sodium bicarbonate, potassium carbonate, sodium carbonate, sodium hydroxide, potassium hydroxide, calcium hydroxide, and the like; amines such as triethylamine, diisopropylethylamine, N-methylmorpholine, pyridine, lutidine, DNU, DBN, DABCO and the like; basic resins and the like. In some embodiments, the base is selected from alkali metal carbonates and alkoxides; such as potassium carbonate or potassium tert-butoxide. The reaction is typically carried out in a temperature range of about 20° C. to about 100° C., from example from about 40° C. to 80° C., or from about 60 to 70° C.

Compound (26) or (26A) can be isolated from the reaction mixture by conventional means, for example, by extraction to obtain two phases, separating the organic layer, and evaporating the organic layer to obtain a residue. Evaporation can be carried out at an elevated temperature of about 45° to about 60° C. and/or a pressure of less than about one atmosphere. The crude product, if necessary, can be purified by any suitable technique, for example, by distillation, crystallization or column chromatography.

After reduction of compound (26) or (26A), for example by hydrogenation using of transition metal such as palladium, rhodium or ruthenium-based reagents, for example, Pd/C, platinum oxide, and the like and deprotection of compound (27), the thus prepared Fingolimod can be transformed in its pharmaceutical salts (e.g., the hydrochloride salt) by methods described in literature, for example EP 0989113, U.S. Pat. No. 6,284,915; and WO 99/01419, the contents of each of which is incorporated by reference herein.

EXPERIMENTAL SECTION

Certain compounds which are representative of this invention were prepared as per the following examples and reaction sequences. No attempt has been made to optimize the yields obtained in any of the reactions. Unless otherwise noted, the materials used in the examples were obtained from readily available commercial suppliers or synthesized by standard methods known to one skilled in the art of chemical synthesis. The work-up treatment in each step can be applied by a typical method, wherein isolation and purification is performed as necessary by selecting or combining conventional methods, such as crystallization, recrystallization, distillation, partitioning, column chromatography, preparative HPLC and the like.

All references disclosed herein are explicitly incorporated by reference in their entirety as if fully set forth herein.

Process 1

Examples 1-5

Example 1

Preparation of 3-nitro-1-(4-octylphenyl)propan-1-one (12)

In a dry flask, 3-nitropropanoic acid [available commercially or prepared according to Silva, P. C.; Costa, J. S.; Pereira, V. L. P. *Synth. Commun.* 2001, 31, 595, (10.0 g, 85.0 mmol) was stirred overnight with $SOCl_2$ (100 ml). Following addition of anhydrous toluene, the solution was azeotropically distilled to remove excess $SOCl_2$. The residue can be used directly for acylation or distilled (80-83° C./0.1-0.2 mbar [SYNTHESIS 2009, No. 5, p. 715]) to afford pure 3-nitropropanoyl chloride as a clear liquid.

$AlCl_3$ (12.0 g, 89.0 mmol) was added to 15 ml of methylene chloride and cooled to 0-5° C., following by addition of 3-nitropropanoyl chloride (11 g, 80 mmol). Octylbenzene (17.10 g, 89.0 mmol) in 40 ml of $CH_2Cl_2$ was dropwise added and the solution was stirred at room temperature under TLC monitoring. After reaction completion, the mixture was poured onto ice, acidified by addition of 2 M HCl to pH 2, and extracted with $CH_2Cl_2$. The combined organic extracts were washed again with 2 M HCl and water, dried over $Na_2SO4$, filtered, and the solvent was removed under reduced pressure to yield a solid that was recrystallized (hexanes) to give 3-nitro-1-phenylpropan-1-one (76%); mp 59-62° C., ESIMS 292 $[M+H]^+$.

Example 2

Preparation of 3-nitro-1-(4-octylphenyl)propyl acetate (13)

To a solution of 3-nitro-1-(4-octylphenyl)propan-1-one (12) (5.00 g) in methanol (25 ml) was added sodium borohydride (0.8 g) at 0° C. and the mixture was left at room temperature for 4.5 hr. The suspension was diluted with ethyl acetate and washed successively with 1 N HCl, sodium bicarbonate solution and brine. The ethyl acetate layer was dried over anhydrous $Na_2SO_4$ and concentrated. To the residue was added pyridine (1.5 eq), dichloromethane (10 v) and acetic anhydride (10 eq), and the mixture was left at room temperature overnight. To the reaction mixture was added ice water and the mixture was extracted with ethyl acetate and washed successively with 1 N HCl, sodium bicarbonate solution and brine. The ethyl acetate solution was dried over sodium sulfate and concentrated. The residue was pure enough for transformation to the next step or can be purified by silica gel column chromatography using hexane-ethyl acetate as eluent. Yield=94%, ESIMS 358.2 $[M+Na]^+$ Example 3

Preparation of 2-nitro-2-[2-(4-octylphenyl)ethyl] propane-1,3-diol (14)

To a mixture of paraformaldehyde (0.13 mol, 9 eq), 4 ml (1.5 eq) of triethylamine in 40 ml of 1,4-dioxane, 3-nitro-1-(4-octylphenyl)propyl acetate (13) (5 g, 0.015 mol) in 50 ml of 1,4-dioxane was added dropwise with stirring at RT, the mixture was slowly heated to 70° C., and stirred for 24 h at this temperature, under TLC control. To the reaction mixture was added water and the mixture, pH adjusted to ~9-10 and stirred 16 h at 40° C. for deprotection (TLC and HPLC monitoring). After reaction completion (~2-3 h) the mixture was extracted with ethyl acetate and washed successively with 1 N HCl, sodium bicarbonate solution and brine. The ethyl acetate solution was dried over sodium sulfate and concentrated. The residue was pure enough for transformation to the next step or can be purified by crystallization or silica gel column chromatography using hexane-ethyl acetate as eluent to afford a white solid with mp. 80-82° C., ESIMS 376.2 $[M+Na]^+$ Example 4

Preparation of 2-amino-2-[2-(4-octylphenyl)ethyl] propane-1,3-diol (Fingolimod)

To 14.1 g (0.04 mol) of 3-(hydroxymethyl)-3-nitro-1-(p-octylphenyl)butane-1,4-diol in 250 ml of methyl alcohol, 30 ml of concentrated hydrochloric acid was added, followed by the catalyst—10% palladium-carbon. The mixture was stirred at 20 kg/cm² hydrogen pressure for two days at room temperature. The mixture was then filtered, methyl alcohol was distilled off, the residue was dissolved in water, adjusted to pH 8 with saturated sodium bicarbonate, and extracted with ethyl acetate (100 ml×3). The ethyl acetate extracts were dried over magnesium sulfate, filtered, evaporated. The residue was dissolved in ethanol (50 ml) and a 1N hydrochloric acid (50 ml) was added thereto. The mixture was stirred for 1 h, the solvent was distilled off and the resultant solid were recrystallized from ethanol to give Fingolimod hydrochloride.

Example 5

Alternative Method for Preparing Fingolimod Hydrochloride from 2-nitro-2-[2-(4-octylphenyl)ethyl]propane-1,3-diol (14)

A. Preparation of (2-nitro-2-(4-octylphenethyl)propane-1,3-diol)

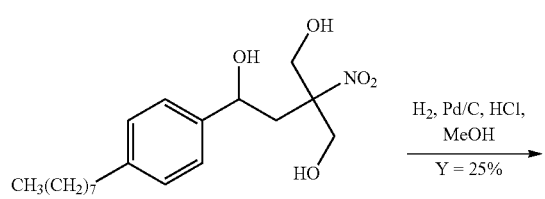

3-(hydroxymethyl)-3-nitro-1-(4-octylphenyl)butane-1,4-diol
Mol. Wt.: 353.45

14

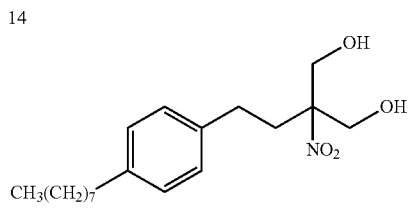

2-nitro-2-(4-octylphenethyl)propane-1,3-diol
Mol. Wt.: 337.45

Procedure:

Compound 14 (0.5 g, 1.4 mmol, 1 eq) was treated with 10% Pd/C (0.3 g. 60% w/w) & conc. HCl (1.2 ml, 48 mmol, 10 eq) in methanol (50 ml, 30 volume) under hydrogen pressure (80 psi) at RT for 20 h. until the starting material disappeared on TLC (solvent system 50% EtOAc in pet ether, product $R_f$=0.7)

Work-Up:

Upon completion of the reaction, Pd/C was removed by filtration through a celite bed then washed with methanol (15 mL×3). Filtrates were concentrated under reduced pressure to obtain the crude residue. Crude residue was reacted with sat. Na$_2$CO$_3$ to adjust pH ~8 then extracted with ethyl acetate (50 mL×4). The organic layer was dried over anhydrous Na$_2$SO$_4$ and evaporated under reduced pressure to obtain the desired product 2-nitro-2-(4-octylphenethyl)propane-1,3-diol.

B. Preparation of (2-amino-2-(4-octylphenethyl)propane-1,3-diol hydrochloride)

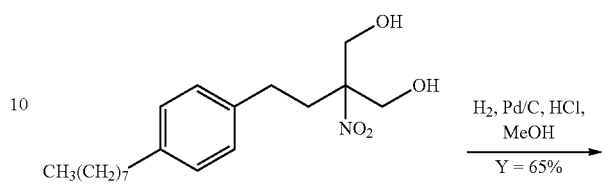

2-nitro-2-(4-octylphenethyl)propane-1,3-diol
Mol. Wt.: 337.45

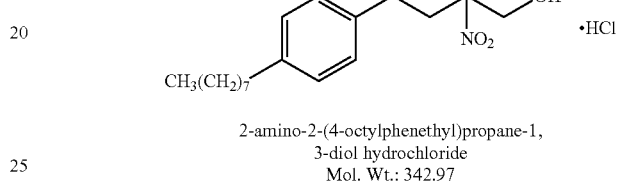

2-amino-2-(4-octylphenethyl)propane-1,3-diol hydrochloride
Mol. Wt.: 342.97

1

Procedure:

2-nitro-2-(4-octylphenethyl)propane-1,3-diol (0.12 g, 0.3 mmol, 1 eq) was treated with 10% Pd/C (0.12 g. 100% w/w) & conc. HCl (1.2 ml, 20 mmol, 67 eq) in methanol (15 ml, 125 volume) under hydrogen pressure (100 psi) at 50° C. for 20 h. until the starting material disappeared on TLC.

Work-Up:

Upon completion of the reaction, Pd/C was removed by filtration through a celite bed then washed with methanol (15 mL×3). Filtrates were concentrated under reduced pressure to obtain the crude residue. Crude residue was dissolved in ethanol (5 ml) at 25-30° C. Hydrochloric acid ether was dropwise into the mixture adjust PH=4. The mixture was reduce pressure under the vacuum at 45-55° C. to get the crude product. The crude product was crystal by Ethanol/Ether (1:4, 2.5 ml) 48 h to get the pure product (80 mg). MS, 1H and 13C-NMR complied with the structure.

Process 2

Examples 6-14

Example 6

Preparation of 3-nitro-1-phenylpropan-1-one (15)

The title compound was prepared from benzene and 3-nitropropanoyl chloride, according to example 2, affording compound (15) with 78% yield, mp 72-74° C.

Example 7

Preparation of 3-nitropropylbenzene (16)

Under an inert atmosphere, 3-nitro-1-phenylpropan-1-one (15) (12.5 g, 70.0 mmol) was dissolved in TFA (100 ml) and Et$_3$SiH (30 ml). This mixture was stirred at room temperature under TLC and GC control. After reaction completion, the mixture was concentrated under reduced pressure and residue was distilled in vacuum to give 3-nitropropylbenzene (16) with 88% yield, bp. 120-123° C./4 mm.

Example 8

Preparation of 1-(4-(3-nitropropyl)phenyl)octan-1-one (17)

The title compound was prepared from 3-nitropropylbenzene (16) and octanoyl chloride, according to example 2, affording compound (17) with 73% yield, which was used at the next step without additional purification.

Example 9

Preparation of 1-(4-(4-hydroxy-3-(hydroxymethyl)-3-nitrobutyl)phenyl)octan-1-one (18)

a) A mixture of 1-(4-(3-nitropropyl)phenyl)octan-1-one (17) (10 mmol) in ethanol (15 ml) and 1,4-dioxane (5 ml), 1 N NaOH (0.05 ml), and 37% aqueous formaldehyde (1.70 ml) was stirred at room temperature overnight. After addition of 37% aqueous formaldehyde (0.50 ml), the mixture was stirred at 50° C. for 5-6 h. The reaction mixture was evaporated and reconstituted with EtOAc. The organic solution was washed with water, brine, dried, and evaporated. The crude compound was transferred for the next step without special purification.

b) Compound (18) was prepared by Henry addition of formaldehyde (37% aqueous solution) to 1-(4-(3-nitropropyl)phenyl)octan-1-one (17) in ethanol, in the presence of strongly basic anion exchange resin Amberlite IRA-401 (OH-), according to the procedure described by Astle and Abbot [J. Org. Chem. 21, 1228 (1956)]. The yield of the desired product was 65%.

Example 10

Preparation of Fingolimod Hydrochloride

The title compound was prepared in 82% yield from 1-(4-(4-hydroxy-3-(hydroxymethyl)-3-nitrobutyl)phenyl)octan-1-one (18) according to example 4.

Example 11

Preparation of 2-nitro-2-phenethylpropane-1,3-diol (19)

Compound (19) was prepared in 72% yield from 3-nitropropylbenzene and formaldehyde, according to example 8b.

Example 12

Preparation of 2,2-dimethyl-5-nitro-5-phenethyl-1,3-dioxane (20)

To a suspension of 2-nitro-2-phenethylpropane-1,3-diol (19) (40.0 mmol) in DMF (40 ml) was added 2,2-dimethoxypropane (6.0 ml, 50 mmol) and p-toluenesulfonic acid monohydrate (400 mg, 2.0 mmol) and stirring was continued overnight. The reaction mixture was diluted with ethyl acetate, washed with saturated $NaHCO_3$ and brine, dried, and concentrated. The residue was pure enough for transformation to the next step or could be purified by silica gel column chromatography.

Example 13

Preparation of 1-(4-(2-(2,2-dimethyl-5-nitro-1,3-dioxan-5-yl)ethyl)phenyl)octan-1-one (21)

The title compound was prepared from 2-dimethyl-5-nitro-5-phenethyl-1,3-dioxane (20) and octanoyl chloride, according to example 2, affording compound (21) with 68% yield, which was used at the next step without additional purification.

Example 14

Preparation of Fingolimod Hydrochloride from Compound (21)

The title compound was prepared in 80% yield from 1-(4-(2-(2,2-dimethyl-5-nitro-1,3-dioxan-5-yl)ethyl)phenyl)octan-1-one (21) according to example 4.

Process 3

Examples 15-17

Example 15

Preparation of tert-Butyl[2,2-Dimethyl-5-(4-octanoylstyryl)-1,3-dioxan-5-yl]carbamate (26, X=O)

Wittig reagent (23, X=O) was prepared from the corresponding bromide and triphenylphosphine in acetone (reflux, 8-10 h).

Phosphonate (25, X=O) was prepared from the corresponding bromide and triethylphosphite (1.5 equiv.) in toluene (reflux, 8-10 h).

tert-Butyl-5-Formyl-2,2-dimethyl-1,3-dioxan-5-ylcarbamate (24) was prepared according to the procedure described by Ooi et al. [J. Org. Chem. 2004, 69, 7765-7768].

A mixture of the Wittig reagent (23, X=O) or the phosphonate (0.3 mmol), aldehyde (24) (0.33 mmol), and $K_2CO_3$ (0.9 mmol) in a mixture of THF (3 ml) and DMF (1 ml) was heated at 70-75° C. under TLC and HPLC monitoring. After completion of the reaction, THF was evaporated and the reaction mixture was quenched with water and then extracted with ethyl acetate. The organic layer was washed with water and brine, dried over $Na_2SO_4$, filtered and concentrated. After purification, the title compound (26) was recovered as white solid with 72% yield, mp 82-83° C.

Example 16

Preparation of tert-butyl 2,2-dimethyl-5-(4-octylstyryl)-1,3-dioxan-5-ylcarbamate (26, X=2H)

Compound (26, X=2H) was prepared from the corresponding Wittig reagent or phosphonate, according to example 13 with 81% yield.

Example 17

Preparation of Fingolimod Hydrochloride from Compound (26)

a) From compound (26, X=O) without separation of intermediate tert-butyl 2,2-dimethyl-5-(4-octylphenethyl)-1,3-dioxan-5-ylcarbamate (27)

Fingolimod hydrochloride was prepared by hydrogenation according to example 4.

b) From compound (26, X═O) with separation of intermediate tert-butyl 2,2-dimethyl-5-(4-octylphenethyl)-1,3-dioxan-5-ylcarbamate (27)

Compound (26, X═O) was reduced by sodium borohydride (2.5-3 equiv.) in methanol at 5-10° C., according to example 2 and then hydrogenated by 10% Pd/C (30 wt %) at room temperature and 1 atm hydrogen pressure for 7-10 h, yielding after filtration of the catalyst and purification, a white solid, mp. 62-64° C.

Compound (26, X=2H) was hydrogenated in the same manner, affording compound (27) as a white solid.

A solution of compound (27) (30 mmol) in $CH_2Cl_2$ (60 ml), TFA (50 ml), and water (30 ml) was stirred at room temperature overnight. The reaction mixture was quenched with $NaHCO_3$ solution and extracted with ethyl acetate. The organic solution was washed with water, brine and dried over $Na_2SO_4$, filtered, and concentrated under vacuum to give the Fingolimod free base (95%) as a white solid, mp 120-124° C. The free base was transformed to its hydrochloride salt according to example 4.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

What is claimed is:

1. A process for the preparation of Fingolimod of formula (I), or a pharmaceutically acceptable salt thereof, comprising the steps of:

a) reacting octylbenzene with a 3-nitropropanoic acid derivative of formula A:

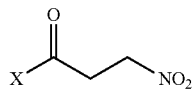

wherein X is a halogen or an anhydride, so as to obtain 3-nitro-1-(4-octylphenyl)propan-1-one of formula (12):

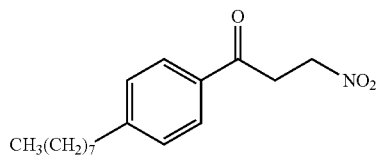

b) reducing 3-nitro-1-(4-octylphenyl)propan-1-one (12) with a reducing agent to obtain 3-nitro-1-(4-octylphenyl)propan-1-ol;

c) protecting the hydroxyl group of 3-nitro-1-(4-octylphenyl)propan-1-ol so as to obtain compound (13A):

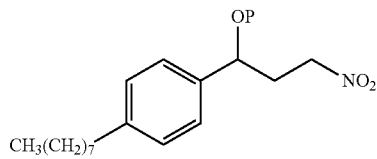

wherein P is a hydroxyl protecting group;

d) bis-hydroxymethylation of compound (13A) with formaldehyde or an equivalent thereof in the presence of catalyst, and removal of the hydroxyl protecting group to obtain compound (14):

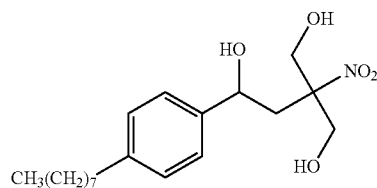

e) reducing compound (14) to Fingolimod (1); and f) optionally, converting Fingolimod (1) to a pharmaceutically acceptable salt thereof.

2. The process according to claim 1, wherein X is Cl.

3. The process according to claim 1, wherein step (a) is conducted in the presence of a Friedel-Crafts catalyst, a metal salt of an organic acid, or a protic acid.

4. The process according to claim 3, wherein
the Friedel Crafts catalyst is selected from $AlCl_3$, $FeCl_3$, $SnCl_4$, $TiCl_4$, $ZnCl_2$ and $BF_3$;
the metal salt of an organic acid is a metal triflate; and
the protic acid is selected from HF, $H_2SO_4$, $CF_3SO_3H$ and an ion-exchange resin.

5. The process according to claim 4, wherein
the metal triflate is hafnium triflate or cerium triflate; or
the ion-exchange resin is Nafion or zeolite.

6. The process according to claim 1, wherein the reducing agent in step (b) is $NaBH_4$.

7. The process according to claim 1, wherein the hydroxy protecting group P in compound (13A) is acetyl ($COCH_3$).

8. The process according to claim 7, wherein in step (c) the protection of 3-nitro-1-(4-octylphenyl)propan-1-ol is carried out by acylation with acetic anhydride or acetyl chloride in the presence of a base.

9. The process according to claim 1, wherein the reduction of 3-nitro-1-(4-octylphenyl)propan-1-one (12) to 3-nitro-1-(4-octylphenyl)propan-1-ol and its conversion to compound (13A) is carried out in one step without isolation of intermediates.

10. The process according to claim 1, wherein in step (d) the bis-hydroxymethylation of compound (13A) is carried out with formaldehyde or paraformaldehyde in the presence of a base.

11. The process according to claim 1, wherein in step (d) the bis-hydroxymethylation of compound (13A) and deprotection to compound (14) is carried out in one step without isolation of intermediates.

12. The process according to claim 1, wherein the reduction step (e) comprises hydrogenating compound (14) to Fingolimod (1) in the presence of a catalyst.

13. The process according to claim 12, wherein the catalyst in step (e) is Pd/C.

14. The process according to claim 1, wherein the pharmaceutically acceptable salt of Fingolimod is the hydrochloride salt.

* * * * *